US010556083B2

(12) United States Patent
Haibach

(10) Patent No.: US 10,556,083 B2
(45) Date of Patent: Feb. 11, 2020

(54) PATIENT INTERFACE DEVICE AND MAINTAINING APPARATUS AND MAINTAINING MEMBER THEREFOR

(71) Applicant: KONINKLIJKE PHILIPS N.V., Eindhoven (NL)

(72) Inventor: Richard Thomas Haibach, Pittsburgh, PA (US)

(73) Assignee: Koninklijke Philips N.V. (NL)

( * ) Notice: Subject to any disclaimer, the term of this patent is extended or adjusted under 35 U.S.C. 154(b) by 504 days.

(21) Appl. No.: 15/345,922

(22) Filed: Nov. 8, 2016

(65) Prior Publication Data

US 2017/0128691 A1    May 11, 2017

Related U.S. Application Data

(60) Provisional application No. 62/253,220, filed on Nov. 10, 2015.

(51) Int. Cl.
*A61M 16/06* (2006.01)

(52) U.S. Cl.
CPC .... *A61M 16/0683* (2013.01); *A61M 16/0611* (2014.02)

(58) Field of Classification Search
CPC .......... A61M 16/0683; A61M 16/0611; A61M 16/0694
See application file for complete search history.

(56) References Cited

U.S. PATENT DOCUMENTS

| 4,136,403 | A | 1/1979 | Walther | |
|---|---|---|---|---|
| 2008/0291277 | A1* | 11/2008 | Jacobsen | G02B 27/0172 348/158 |
| 2009/0145444 | A1 | 6/2009 | Edwards | |
| 2011/0125238 | A1 | 5/2011 | Nofzinger | |
| 2014/0246024 | A1 | 9/2014 | Cragg | |
| 2014/0261436 | A1* | 9/2014 | McCaslin | A61M 16/0666 128/205.25 |

* cited by examiner

Primary Examiner — Theodore J Stigell
(74) Attorney, Agent, or Firm — Michael W. Haas

(57) ABSTRACT

A maintaining member is for a patient interface device. The patient interface device includes a cushion member structured to engage a face of a patient. The maintaining member has body structured to be located on a single side of the face of the patient. The body includes a coupling portion structured to be coupled to the cushion member, and a maintaining portion extending from the coupling portion, the maintaining portion having a receiving portion located opposite and facing the coupling portion, the receiving portion being concave facing in a direction toward the coupling portion in order to maintain the patient interface device on the face of the patient.

15 Claims, 6 Drawing Sheets

PATIENT INTERFACE DEVICE AND MAINTAINING APPARATUS AND MAINTAINING MEMBER THEREFOR

CROSS-REFERENCE TO RELATED APPLICATIONS

This patent application claims the priority benefit under 35 U.S.C. § 119(e) of U.S. Provisional Application No. 62/253,220 filed on Nov. 10, 2015, the contents of which are herein incorporated by reference.

BACKGROUND OF THE INVENTION

1. Field of the Invention

The present invention relates to patient interface devices used to deliver a flow of breathing gas to a patient. The present invention also relates to maintaining apparatuses and maintaining members for patient interface devices.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a pillows style mask wherein a nasal cushion has nasal prongs that are received within the patient's nares, a nasal/oral mask that covers the nose and mouth, or a full face mask that covers the patient's face. The patient interface device is connected to a gas delivery hose and interfaces the ventilator or pressure support device with the airway of the patient, so that a flow of breathing gas can be delivered from the pressure/flow generating device to the airway of the patient.

It is known to maintain such devices on the face of the patient by way of a headgear having one or more straps adapted to fit over/around the patient's head. Employing headgear straps often results in a feeling of claustrophobia for the patient. For example, the headgear straps typically pull the mask component onto the patient's face, such that the only practical way to remove the mask component is to unfasten the straps.

SUMMARY OF THE INVENTION

Accordingly, it is an object of the present invention to provide a maintaining member for a patient interface device. The patient interface device includes a cushion member structured to engage a face of a patient. The maintaining member comprises a body structured to be located on a single side of the face of the patient, the body comprising a coupling portion structured to be coupled to the cushion member, and a maintaining portion extending from the coupling portion, the maintaining portion having a receiving portion located opposite and facing the coupling portion, the receiving portion being concave facing in a direction toward the coupling portion in order to maintain the patient interface device on the face of the patient.

It is yet another object of the present invention to provide a maintaining apparatus for a patient interface device including a cushion member structured to engage a face of a patient. The maintaining apparatus comprises a maintaining member and a fabric member coupled to the maintaining member. The fabric member is structured to engage the face of the patient.

It is yet a further object of the present invention to provide a patient interface device comprising a cushion member and a maintaining apparatus comprising a maintaining member. The coupling portion of the maintaining member is coupled to the cushion member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a," "an," and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled"

means that two elements are directly in contact with each other. As used herein, the phrase "removably coupled" means that one component is coupled with another component in an essentially temporary manner. That is, the two components are coupled in such a way that the joining or separation of the components is easy and would not damage the components. For example, two components secured to each other by a press-fit mechanism or a snap-fit mechanism are "removably coupled" whereas two components that involve welding processes, glue, or fasteners to be joined are not "removably coupled."

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the term "fabric" shall mean a material consisting of a network of interlaced or otherwise entangled natural or artificial fibers made by, for example and without limitation, weaving, knitting, spreading, crocheting, or bonding (e.g., by chemical, mechanical, heat or solvent treatment) the fibers to form the network, and may include, for example, and without limitation, woven and nonwoven fabric materials.

As used herein, the term "spherical concavity" shall mean concave in two perpendicular planes. For example and without limitation, a partially spherical-shaped member has spherical concavity by virtue of having the member be curved in two perpendicular planes. By contrast, a partially cylindrical-shaped member does not have spherical concavity because the member is curved in only one single plane.

Figure 1:
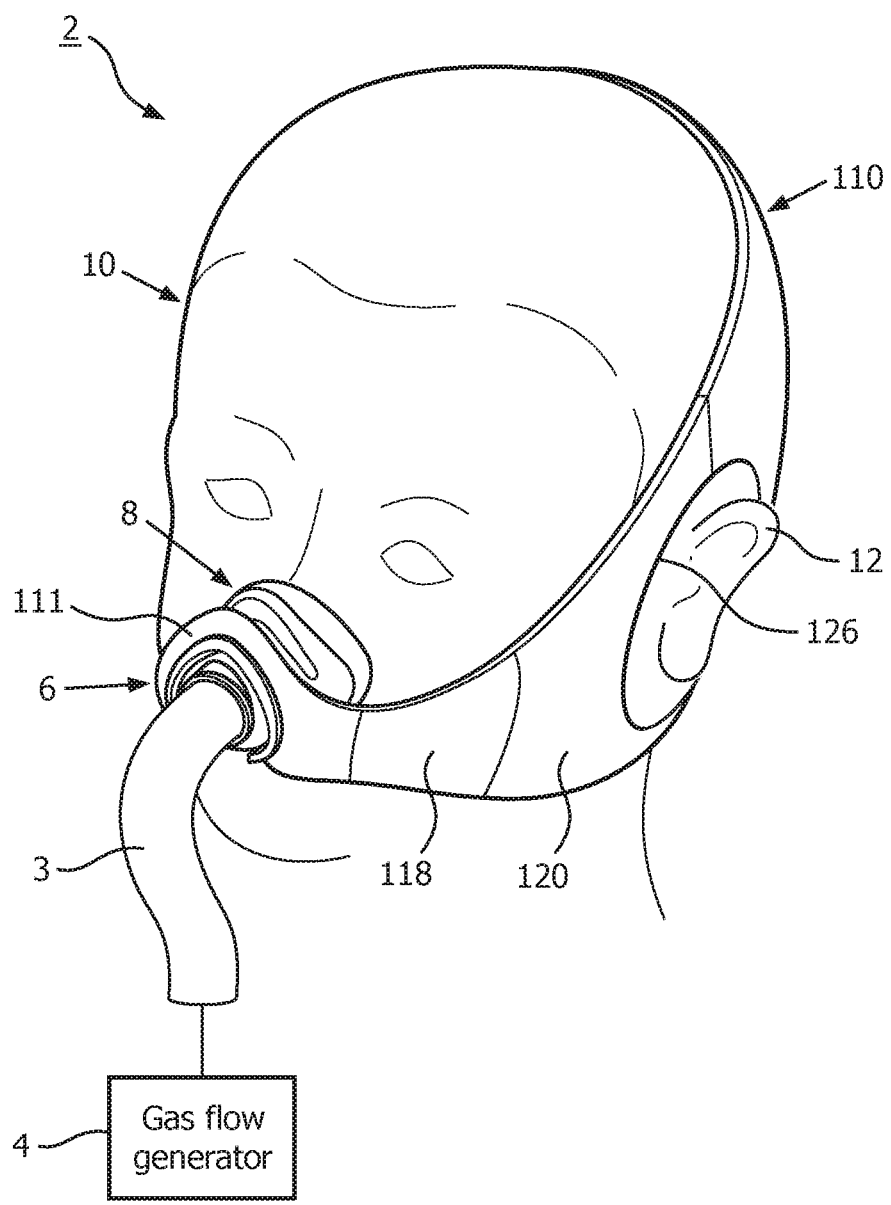
FIG. 1 is a front isometric view of a pressure support system including a patient interface device, shown as employed on a patient and with portions removed in order to see hidden structures, in accordance with a non-limiting embodiment of the disclosed concept.

FIG. 1 shows a pressure support system 2 in accordance with a non-limiting embodiment of the disclosed concept. Pressure support system 2 includes a gas delivery conduit (e.g., without limitation, hose 3, shown in simplified form), a gas flow generator 4 (shown in simplified form), and a patient interface device 6. Patient interface device 6 includes a cushion member 8 and a maintaining apparatus. In the exemplary embodiment, the maintaining apparatus is shown in FIG. 1 in the form of a maintaining member 110. Hose 3 fluidly couples gas flow generator 4 to patient interface device 6 in order to allow gas flow generator 4 to deliver a flow of breathing gas to an airway of a patient 10. As will be discussed in greater detail hereinbelow, maintaining member 110 is a body that is advantageously structured to maintain engagement between cushion member 8 and patient 10 without a separate fastening member, thereby resulting in a relatively reduced claustrophobic feeling for patient 10 when patient interface device 6 is donned. This is distinct from a typical prior art patient interface device (not shown) in which a cushion member is structured to be secured to a patient in a manner wherein the only way to remove the patient interface device is for the patient to unfasten a separate retention member, such as a headgear strap.

Figure 2:
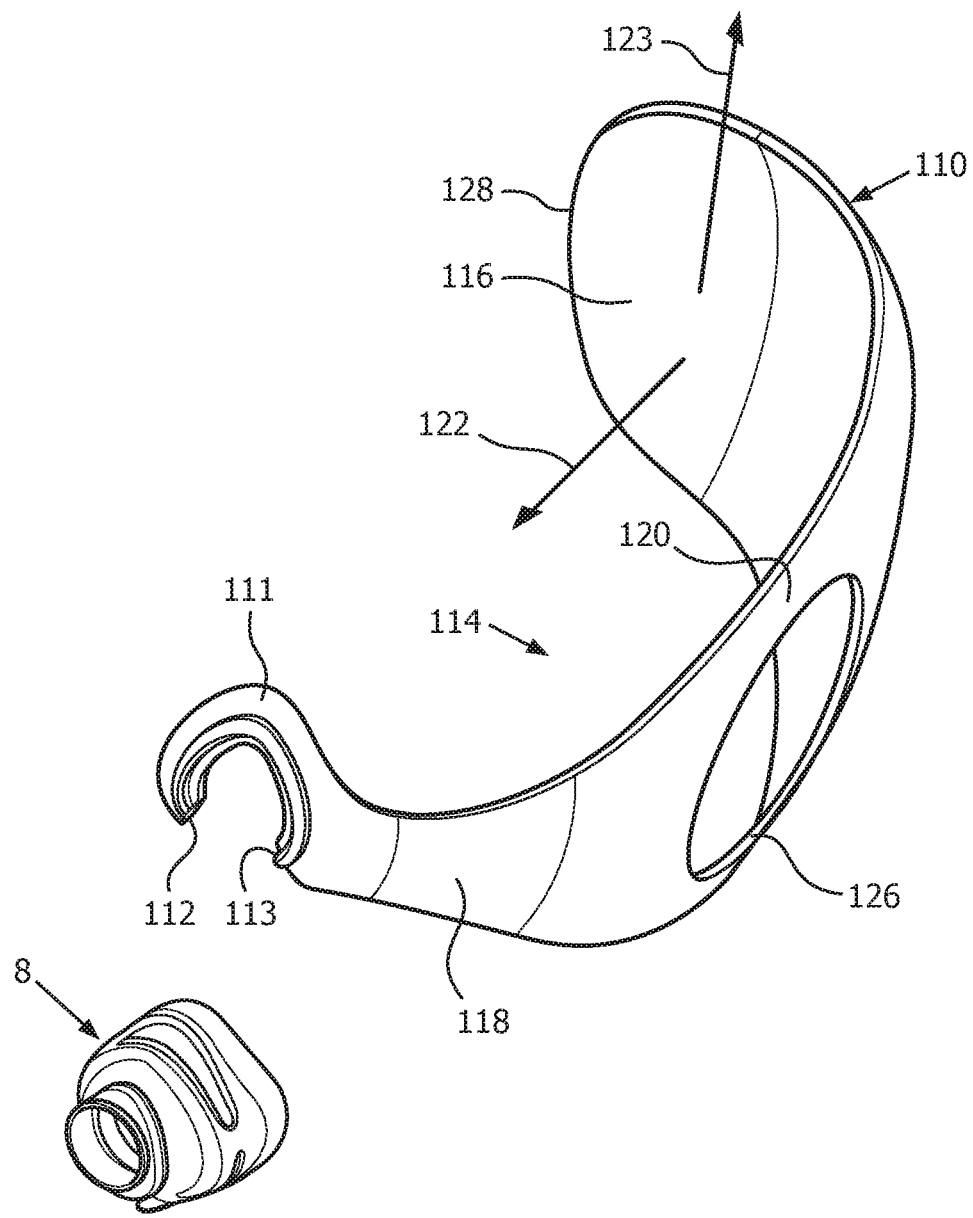
FIG. 2 is an exploded front isometric view of a cushion member and a maintaining member for the patient interface device of FIG. 1.

FIG. 2 shows an exploded view of cushion member 8 and maintaining member 110. Maintaining member 110 includes a C-shaped coupling portion 111 structured to be coupled to cushion member 8, and a maintaining portion 114 extending from coupling portion 111. Coupling portion 111 has a first distal portion 112 and a second distal portion 113 each being structured to engage cushion member 8. When coupling portion 111 is pressed onto cushion member 8 during assembly of patient interface device 6, first distal portion 112 and second distal portion 113 initially move (e.g., flex) away from one another, and then move toward one another in order to allow maintaining member 110 to be coupled to cushion member 8 by a snap-fit mechanism. Maintaining member 110 is structured to be located on a single side of the face of patient 10. That is, maintaining member 110 has a first terminal end proximate coupling portion 111 and the mouth of patient 10, and a second, opposite terminal end proximate receiving portion 116 and the back of the head of patient 10. In this manner, maintaining member 110 is generally semi-circular shaped, or is structured to have about 180 degrees of rotation. As a result, donning and removing patient interface device 6 is significantly easier as compared to prior art patient interface devices, as will be discussed herein.

Figure 3:
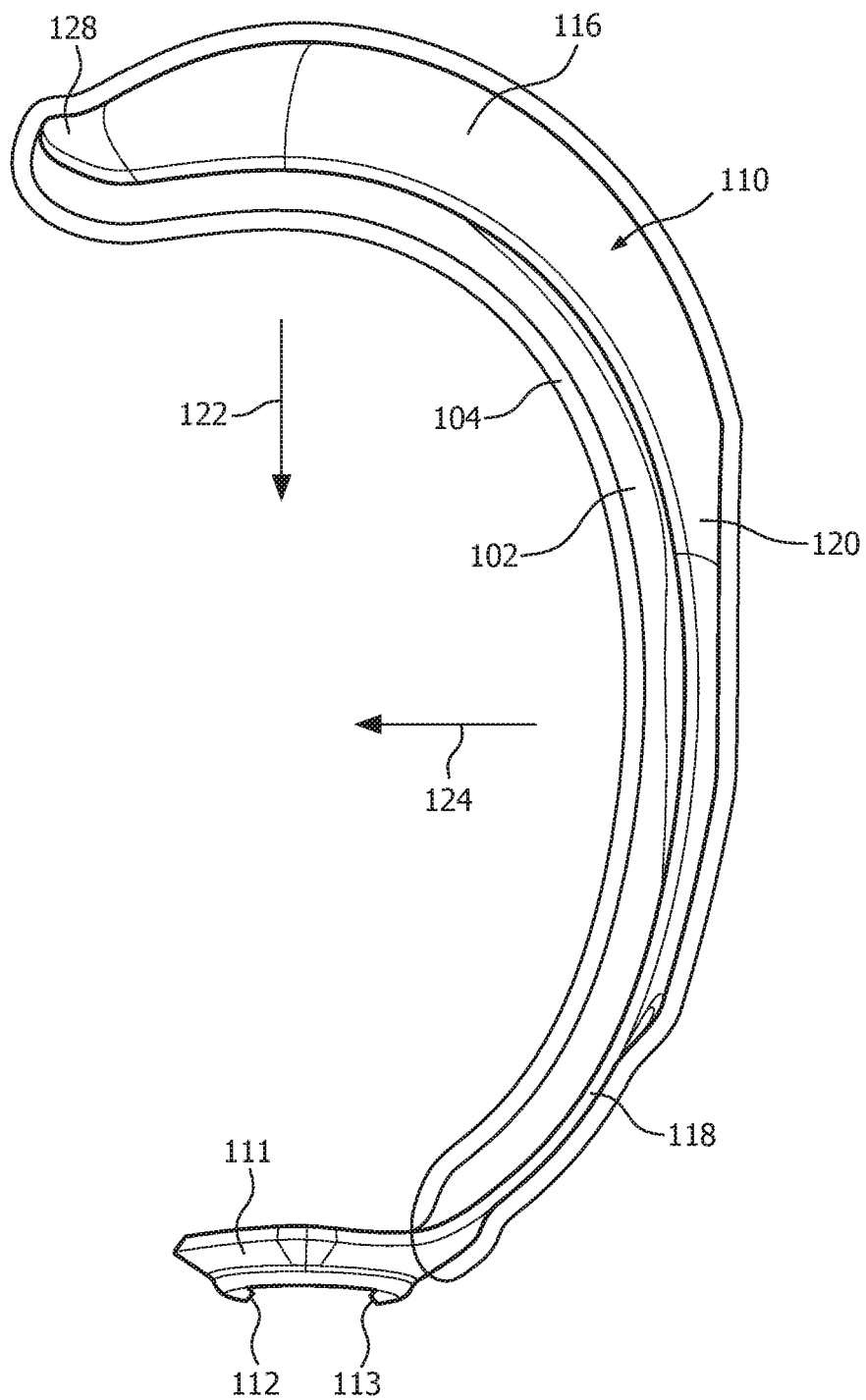
FIG. 3 is a top plan view of a maintaining apparatus for the patient interface device of FIG. 1.

Maintaining portion 114 includes a receiving portion 116, a biasing portion 118 extending from coupling portion 111, and a support portion 120 extending from receiving portion 116 to biasing portion 118. Referring to FIG. 3, receiving portion 116 has generally spherical concavity facing in a direction 122 toward coupling portion 111. In this manner, receiving portion 116 is structured to receive the back of the head of patient 10 and prevent movement of patient 10 in direction 122 and in a direction opposite direction 122. Additionally, referring to FIG. 2, because receiving portion 116 has generally spherical concavity, receiving portion 116 is also structured to prevent movement of patient 10 in a direction 123 that is perpendicular to direction 122. Furthermore, support portion 120 has generally spherical concavity facing in a direction 124 perpendicular to direction 122, and between coupling portion 111 and receiving portion 116. It will, however, be appreciated that a similar suitable alternative maintaining member (not shown) may have a receiving portion and/or a support portion with alternative concave natures (e.g., without limitation, having curvature in only one single plane), without departing from the scope of the disclosed concept.

Support portion 120 has an edge portion 126 defining a thru hole in order to receive an ear 12 (FIG. 1) of patient 10. As shown in FIG. 3, in the exemplary embodiment, the maintaining apparatus further includes a foam member 102 (shown in simplified form) and a fabric member 104 (shown in simplified form) coupled to foam member 102 and maintaining member 110. In the exemplary embodiment, foam member 102 is directly coupled to maintaining member 110 and is located between fabric member 104 and maintaining member 110. Fabric member 104, which substantially encapsulates foam member 102 and maintaining member 110, is structured to engage the face of patient 10. Additionally, when patient interface device 6 is donned by patient 10, foam member 102 is structured to deflect and thereby provide a relatively comfortable pillow-like experience for patient 10. Furthermore, fabric member 104 is removably coupled to foam member 102 by any suitable mechanism known in the art. In this manner, patient interface device 6 is advantageously able to remain clean after repeated use. More specifically, patient 10 simply needs to remove and wash the separable fabric member 104, and re-couple fabric member 104 to patient interface device 6.

Figure 4:
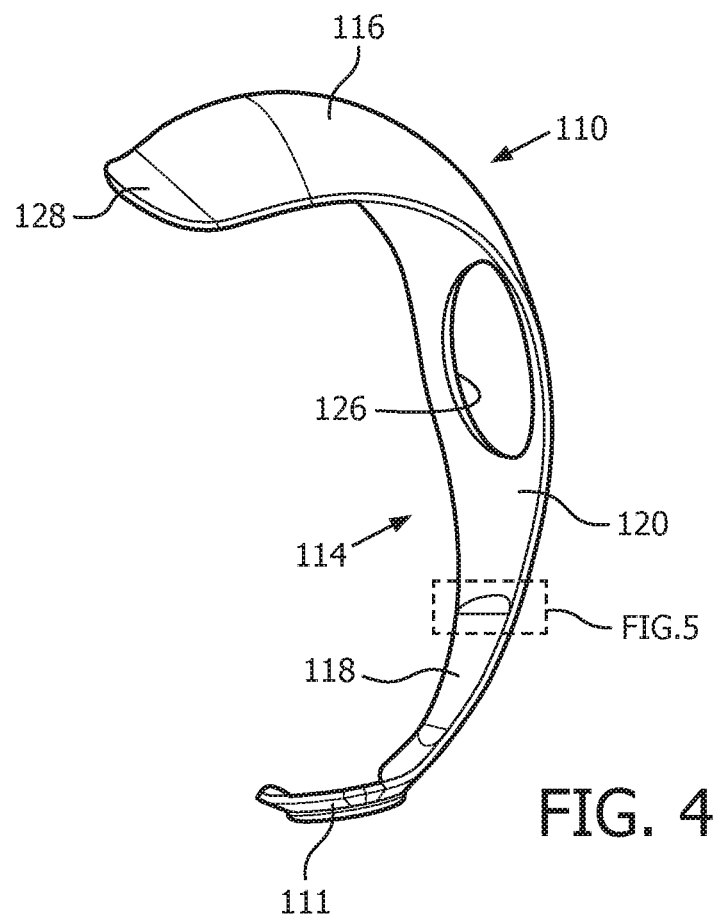
FIG. 4 is a front isometric view of the maintaining member for the patient interface device of FIG. 1.
Figure 5:
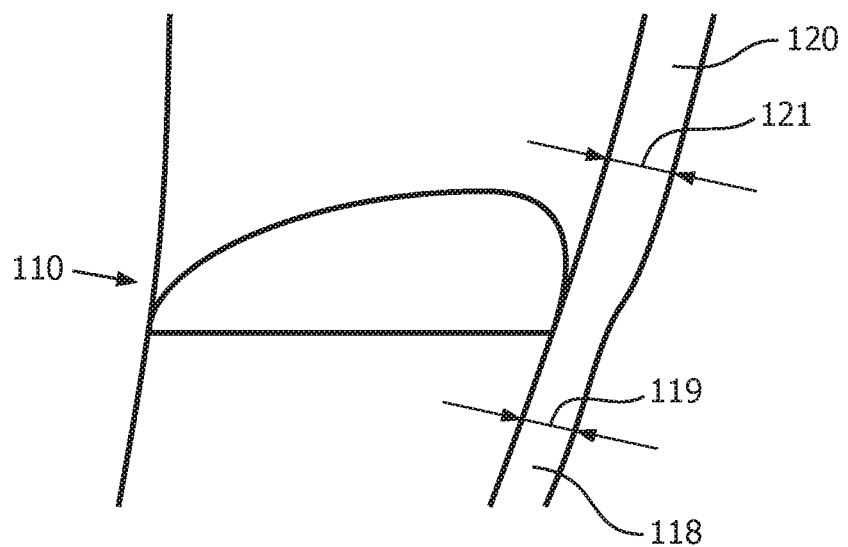
FIG. 5 is an enlarged view of a portion of the maintaining member of FIG. 4.

Referring to FIG. 4, although receiving portion 116 and support portion 120 have generally spherical concavity, biasing portion 118 is generally flat. Biasing portion 118 also has a relatively small thickness. As shown in FIG. 5, biasing portion 118 has a first thickness 119 and support portion 120 has a second thickness 121 greater than first thickness 119.

In one embodiment second thickness 121 is at least 10 percent, or 1.1 times thicker than first thickness 119. In this manner, when patient interface device 6 is donned by patient 10, by being generally flat and having a relatively small thickness 119, biasing portion 118 is structured to operate as a pivot point to allow maintaining member 110 to be biased toward engagement with the face of patient 10.

Additionally, in the exemplary embodiment, maintaining member 110 is a unitary member made of a relatively rigid material. For example and without limitation, maintaining member 110 may be a thermoplastic member having a modulus of elasticity greater than 200 megapascals or may be a foam member having an indentation force deflection value of at least 40 pounds per 50 square inches at a compression depth of 25 percent. Maintaining member 110 may thus be manufactured by any suitable mechanism known in the art (e.g., without limitation, thermoformed, printed with a three-dimensional printer, and/or injection molded) in order to have the desired rigidity. It will also be appreciated that custom methods may be employed to manufacture maintaining member 110. For example, an imaging device such as a three-dimensional scanner may be employed to scan the face of the patient, and data may be sent to a three-dimensional printer based on the facial scan in order to print a customized maintaining member.

Furthermore, by being made of a relatively rigid material, when maintaining member 110 is deflected, an elastic force is exerted by maintaining member 110 toward its original position. In this manner, and as a result of the spherical concavity of receiving portion 116 and support portion 120, and the relatively flat and thin nature of biasing portion 118, maintaining member 110 is advantageously able to maintain patient interface device 6 on the face of patient 10. More specifically, receiving portion 116 and support portion 120 have a cupping nature that is structured to prevent independent movement of patient interface device 6 with respect to patient 10. Biasing portion 118 is structured to force patient interface device 6 into engagement with patient 10 by virtue of its relatively flat and thin nature. In this manner, in addition to maintaining patient interface device 6 on the face of patient 10, maintaining member 110 is structured to maintain patient interface device 6 on the face of a number of other patients with different head structures than patient 10. Stated differently, patients with different head sizes can each don patient interface device 6 and rely on the concavity of receiving portion 116 and support portion 120, and the relatively flat and thin biasing portion 118 to prevent patient interface device 6 from disengaging when pressure support therapy is being delivered.

In one exemplary embodiment, maintaining portion 114 further includes a distal portion 128 extending from receiving portion 116 radially outwardly with respect to and away from coupling portion 111. Distal portion 128 is advantageously structured to allow patient 10 to don patient interface device 6 by providing a relatively smooth transition portion to the rest of maintaining portion 114. That is, distal portion 128 operates as a first contact portion that allows the head of patient 10 to smoothly slide into receiving portion 116. Because distal portion 128 extends radially outwardly with respect to coupling portion 111, the force exerted on the head of patient 10 by distal portion 128 when patient interface device 6 is initially being donned is such that continued movement of the head of patient 10 toward installation, and eventual full installation, is simplified rather than inhibited.

When patient interface device 6 is donned by patient 10, maintaining member 110 is reliably maintained on the face of patient 10 in a removable manner such that relatively small amounts of effort are required for patient interface device 6 to be removed. Example efforts for patient 10 include simply raising his or her head out of patient interface device 6, or exerting a relatively small force on distal portion 128 to move distal portion 128 radially outwardly with respect to coupling portion 111. This is distinct from prior art patient interface devices (not shown) which typically require headgear straps to be unstrapped in order to free the patient from the patient interface device. Accordingly, when patient interface device 6 is donned, rather than wearing patient interface device 6, patient 10 is laying on patient interface device 6. As a result of the ease of removability, the likelihood of undesirable feelings of claustrophobia for patient 10 when patient interface device 6 is donned is significantly minimized.

Thus, patient interface device 6 is advantageously well suited for side sleeping. More specifically, by relying on the weight of the head of patient 10 and a normal force supplied by a pillow, patient interface device 6 is reliably maintained on the face of patient 10 when pressure support therapy is being delivered. As shown in FIG. 3, distal portion 128 is structured to be located slightly on an opposing side of the head of patient 10 as compared to support portion 120, a configuration that makes patient interface device 6 also well suited for back sleeping. It will however be appreciated that a similar suitable alternative maintaining member (not shown) may have a distal portion structured to be located at a midpoint of the back of the head of the patient, without departing from the scope of the disclosed concept.

Figure 6:
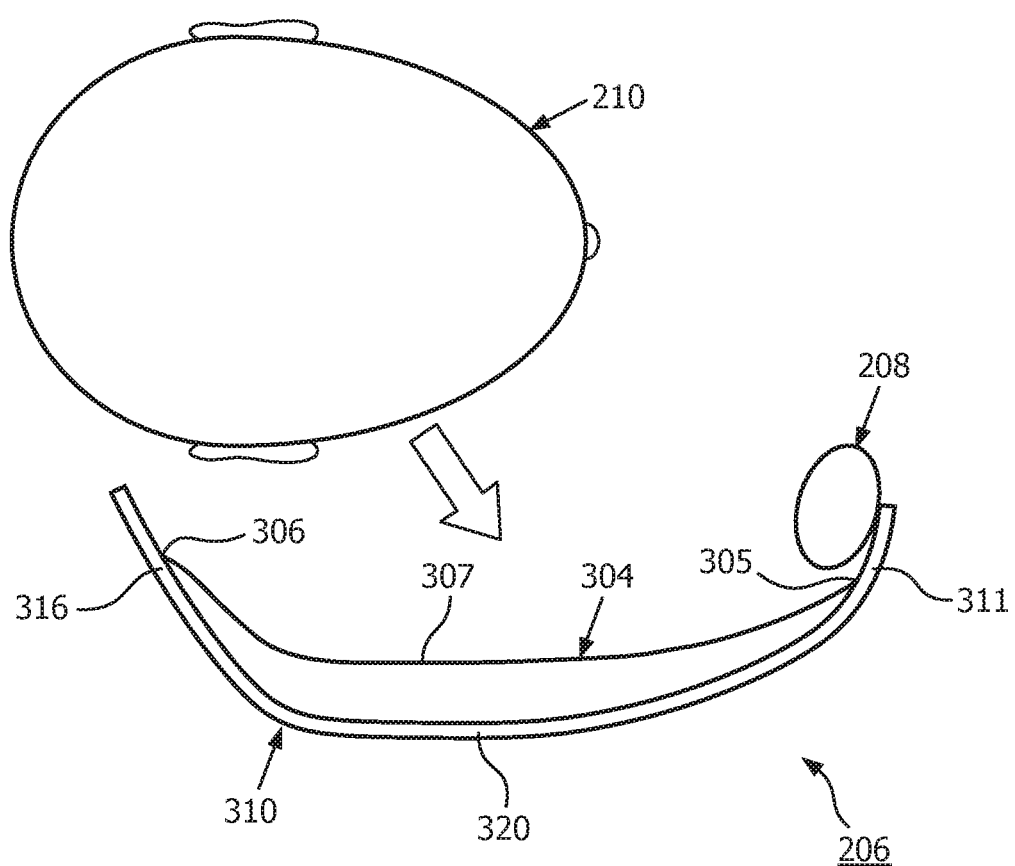
FIG. 6 is a simplified view of another patient interface device, shown as employed with a patient and before being donned by the patient, in accordance with another non-limiting embodiment of the disclosed concept.

FIG. 6 shows a simplified view of an alternative patient interface device 206 in accordance with another non-limiting embodiment of the disclosed concept. Patient interface device 206 includes a cushion member 208 and a maintaining apparatus coupled to cushion member 208. In this embodiment, the maintaining apparatus is illustrated in the form of a maintaining member 310 and a fabric member 304 coupled to maintaining member 310. As shown, fabric member 304 has a first connecting portion 305, a second connecting portion 306 located opposite first connecting portion 305, and a body portion 307 extending between first and second connecting portions 305, 306. First connecting portion 305 is connected to a coupling portion 311 of maintaining member 310 and second connecting portion 306 is connected to a receiving portion 316 of maintaining member 310. As shown in the depicted first position of FIG. 6, in which the head of a patient 210 is spaced from patient interface device 206, body portion 307 is spaced from a support portion 320 of maintaining member 310. However, body portion 307 is structured to move between the first position shown in FIG. 6 and a second position corresponding to patient interface device 206 being donned by patient 210. When patient 210 dons patient interface device 206, body portion 307 is structured to move toward support portion 320 in order to pull receiving portion 316 and coupling portion 311 toward one another. In this manner, fabric member 304 advantageously operates as a tension member for patient interface device 206. That is, patient interface device 206 is able to be maintained on the face of patient 210 at least in part by virtue of fabric member 304 pulling receiving portion 316 and coupling portion 311 toward one another, and thus toward engagement with head of patient 210.

Figure 7A:
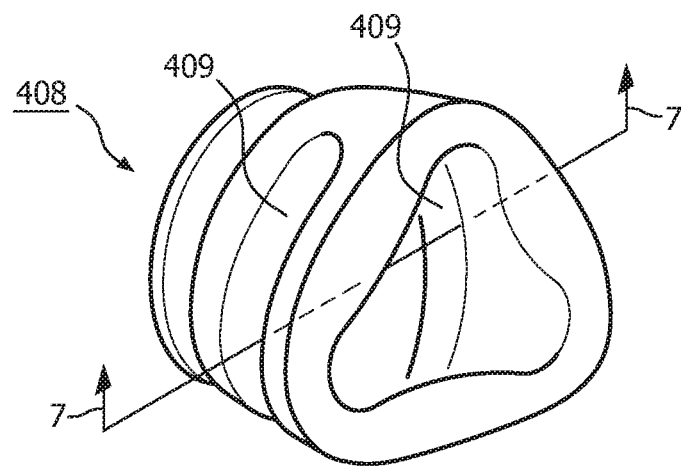
FIG. 7A is a front isometric view of another cushion member, in accordance with another non-limiting embodiment of the disclosed concept.
Figure 7B:
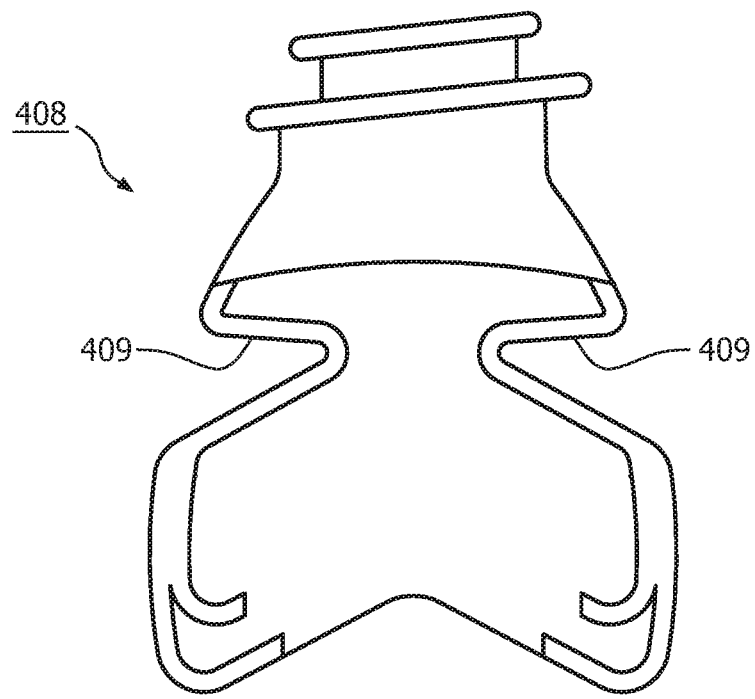
FIG. 7B is a section view of the cushion member of FIG. 7A, taken along line 7-7 of FIG. 7A.

FIGS. 7A and 7B show front isometric and section views, respectively, of an alternative cushion member 408 that may replace either of cushion members 8, 208 in patient interface devices 6, 206, discussed hereinabove. As shown, cushion member 408 includes a number of bellows portions 409. When cushion member 408 is coupled to a respective one of maintaining members 110, 310, a respective one of coupling portions 111, 311 is structured to engage bellows portions 409. By having bellows portions 409, cushion member 408 is structured to be relatively flexible. In this manner, when a respective coupling portion 111, 311 is coupled to bellows portions 409, cushion member 408 can move side to side. Accordingly, when pressure support therapy is being delivered to one of patients 10, 210, movement of patient 10, 210 will advantageously not result in cushion member 408 being dislodged.

Although the disclosed concept has been described in association with nasal cushion members 8, 208, 408, it will be appreciated that maintaining members 110, 310, or similar suitable alternative maintaining members (not shown), may be employed with any cushion member type (e.g., without limitation, cradle style, pillows style, full face) without departing from the scope of the disclosed concept. Additionally, although the disclosed concept has been described in association with biasing portion 118 extending from coupling portion 111 proximate the mouth of patient 10, it is within the scope of the disclosed concept for a similar suitable alternative maintaining member (not shown) to have a similar biasing portion, but wherein the biasing portion is located proximate the ear or back of the head of the patient, thereby moving the pivot point to either the ear or back of the head of the patient. It is also within the scope of the disclosed concept for a similar suitable alternative maintaining member to not include a biasing portion.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A maintaining member for a patient interface device, the patient interface device comprising a cushion member structured to engage a face of a patient to deliver a flow of breathing gas to an airway of the patient, the maintaining member comprising:
    a body structured to be disposed on a single side of the face of the patient, the single side of the face of the patient being either a left side of the face or a right side of the face, the body comprising:
        a coupling portion structured to be coupled to the cushion member; and
        a maintaining portion extending from the coupling portion, the maintaining portion having a receiving portion disposed opposite and facing the coupling portion, the receiving portion being structured to be disposed on a back side of a head of the patient and being concave facing in a direction toward the coupling portion in order to maintain the patient interface device on the face of the patient.

2. The maintaining member according to claim 1, wherein the maintaining portion further has a biasing portion and a support portion, wherein the biasing portion extends from the coupling portion, wherein the support portion extends from the biasing portion to the receiving portion, and wherein the biasing portion is structured to bias the maintaining member toward engagement with the face of the patient.

3. The maintaining member according to claim 2, wherein the biasing portion is flat.

4. The maintaining member according to claim 2, wherein the biasing portion has a first thickness, and wherein the support portion has a second thickness greater than the first thickness.

5. The maintaining member according to claim 1, wherein the receiving portion has generally spherical concavity facing in a first direction toward the coupling portion.

6. The maintaining member according to claim 5, wherein the maintaining portion further has a support portion extending from the receiving portion, and wherein the support portion has generally spherical concavity facing in a second direction perpendicular to the first direction.

7. The maintaining member according to claim 1, wherein the maintaining portion has a support portion extending from the receiving portion, and wherein the support portion has an edge portion defining a thru hole in order to receive an ear of the patient.

8. The maintaining member according to claim 1, wherein the maintaining portion further has a distal portion extending from the receiving portion radially outwardly with respect to the coupling portion.

9. The maintaining member according to claim 1, wherein the body is selected from the group consisting of a thermoplastic member having a modulus of elasticity greater than 200 megapascals and a foam member having an indentation force deflection value of at least 40 pounds per 50 square inches at a compression depth of 25 percent.

10. A maintaining apparatus for the patient interface device of claim 1, the maintaining apparatus comprising:
    the maintaining member according to claim 1; and
    a fabric member coupled to the maintaining member, the fabric member being structured to engage the face of the patient.

11. The maintaining apparatus according to claim 10, wherein the maintaining portion further has a support portion extending from the receiving portion toward the coupling portion, wherein the fabric member includes:
    a first connecting portion,
    a second connecting portion disposed opposite the first connecting portion, and
    a body portion extending between the first connecting portion and the second connecting portion, wherein the first connecting portion is connected to the coupling portion, wherein the second connecting portion is connected to the receiving portion, wherein the body portion is structured to move between a first position and a second position, wherein, when the body portion is in the first position, the body portion is spaced from the support portion, and wherein, when the body portion moves from the first position toward the second position, the body portion moves toward the support portion in order to pull the receiving portion and the coupling portion toward one another.

12. The maintaining apparatus according to claim 10, further comprising a foam member directly coupled to the maintaining member, and wherein the foam member is disposed between the fabric member and the maintaining member.

13. A patient interface device comprising:
a cushion member; and
a maintaining apparatus comprising the maintaining member according to claim 1, the coupling portion of the maintaining member being coupled to the cushion member.

14. The patient interface device according to claim 13, wherein the cushion member comprises a number of bellows portions structured to engage the coupling portion.

15. A patient interface device comprising:
a cushion member; and
a maintaining apparatus comprising a maintaining member, the maintaining member comprising:
a body structured to be disposed on a single side of the face of the patient, the body comprising:
a coupling portion coupled to the cushion member; and
a maintaining portion extending from the coupling portion, the maintaining portion having a receiving portion disposed opposite and facing the coupling portion, the receiving portion being concave facing in a direction toward the coupling portion in order to maintain the patient interface device on the face of the patient, and
wherein the coupling portion has a first distal portion and a second distal portion each being structured to engage the cushion member, and wherein the first distal portion and the second distal portion are structured to move both away from one another and toward one another in order to allow the maintaining member to be coupled to the cushion member by a snap-fit mechanism.

* * * * *